(12) United States Patent
Kahn et al.

(10) Patent No.: US 7,753,861 B1
(45) Date of Patent: Jul. 13, 2010

(54) CHEST STRAP HAVING HUMAN ACTIVITY MONITORING DEVICE

(75) Inventors: Philippe Kahn, Aptos, CA (US); Arthur Kinsolving, Santa Cruz, CA (US); Mark Andrew Christensen, Santa Cruz, CA (US); Brian Y Lee, Aptos, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 11/732,949

(22) Filed: Apr. 4, 2007

(51) Int. Cl.
*A63B 71/00* (2006.01)
*A61B 5/00* (2006.01)
*A61B 5/103* (2006.01)
*A61B 5/117* (2006.01)

(52) U.S. Cl. .............. 600/595; 482/8; 482/9; 600/300; 600/301; 600/587

(58) Field of Classification Search ............. 482/8; 600/300–301, 508, 587, 595
See application file for complete search history.

(56) References Cited

U.S. PATENT DOCUMENTS

| | | | | |
|---|---|---|---|---|
| 4,285,041 | A | * | 8/1981 | Smith ............................ 482/3 |
| 4,578,769 | A | | 3/1986 | Frederick |
| 5,446,725 | A | | 8/1995 | Ishiwatari |
| 5,446,775 | A | | 8/1995 | Wright et al. |
| 5,593,431 | A | * | 1/1997 | Sheldon ....................... 607/19 |
| 5,654,619 | A | | 8/1997 | Iwashita |
| 5,778,882 | A | | 7/1998 | Raymond et al. |
| 5,955,667 | A | | 9/1999 | Fyfe |
| 5,976,083 | A | | 11/1999 | Richardson et al. |
| 6,135,951 | A | * | 10/2000 | Richardson et al. ......... 600/300 |
| 6,145,389 | A | | 11/2000 | Ebeling et al. |
| 6,282,496 | B1 | | 8/2001 | Chowdhary |
| 6,369,794 | B1 | | 4/2002 | Sakurai et al. |
| 6,428,490 | B1 | * | 8/2002 | Kramer et al. .............. 600/595 |
| 6,493,652 | B1 | | 12/2002 | Ohlenbusch et al. |
| 6,513,381 | B2 | | 2/2003 | Fyfe et al. |
| 6,522,266 | B1 | | 2/2003 | Soehren et al. |
| 6,532,419 | B1 | | 3/2003 | Begin et al. |
| 6,539,336 | B1 | | 3/2003 | Vock et al. |
| 6,700,499 | B2 | | 3/2004 | Kubo et al. |
| 6,790,178 | B1 | | 9/2004 | Mault et al. |
| 6,813,582 | B2 | | 11/2004 | Levi et al. |
| 6,823,036 | B1 | | 11/2004 | Chen |
| 6,826,477 | B2 | | 11/2004 | Ladetto et al. |

(Continued)

OTHER PUBLICATIONS

"Wearable Health Reports", Technology Review, Feb. 28, 2006 http://www.techreview.com/printer_friendly_article.aspx?id+16431, Mar. 22, 2007 3 pages.

(Continued)

*Primary Examiner*—Max Hindenburg
*Assistant Examiner*—Sean P Dougherty
(74) *Attorney, Agent, or Firm*—Blakely, Sokoloff, Taylor & Zafman, LLP; Judith A. Szepesi

(57) ABSTRACT

A method for monitoring human activity using an inertial sensor includes monitoring accelerations from an inertial sensor disposed in a chest strap. The accelerations are processed to determine one or more acceleration statistics. The acceleration statistics are formatted to a generic format understandable by a plurality of devices. The formatted acceleration statistics are then transmitted.

20 Claims, 14 Drawing Sheets

U.S. PATENT DOCUMENTS

| | | |
|---|---|---|
| 6,836,744 B1 | 12/2004 | Asphahani et al. |
| 6,881,191 B2 | 4/2005 | Oakley et al. |
| 6,885,971 B2 | 4/2005 | Vock et al. |
| 6,898,550 B1 | 5/2005 | Blackadar et al. |
| 6,928,382 B2 * | 8/2005 | Hong et al. .................. 702/141 |
| 6,941,239 B2 | 9/2005 | Unuma et al. |
| 6,959,259 B2 | 10/2005 | Vock et al. |
| 6,975,959 B2 | 12/2005 | Dietrich et al. |
| 7,072,789 B2 | 7/2006 | Vock et al. |
| 7,092,846 B2 | 8/2006 | Vock et al. |
| 7,148,797 B2 | 12/2006 | Albert |
| 7,158,912 B2 | 1/2007 | Vock et al. |
| 7,169,084 B2 | 1/2007 | Tsuji |
| 7,171,331 B2 | 1/2007 | Vock et al. |
| 7,200,517 B2 | 4/2007 | Darley et al. |
| 7,212,943 B2 | 5/2007 | Aoshima et al. |
| 7,220,220 B2 | 5/2007 | Stubbs et al. |
| 7,297,088 B2 | 11/2007 | Tsuji |
| 7,353,112 B2 | 4/2008 | Choi et al. |
| 7,387,611 B2 * | 6/2008 | Inoue et al. .................. 600/595 |
| 7,457,719 B1 | 11/2008 | Kahn et al. |
| 7,526,402 B2 | 4/2009 | Tanenhaus et al. |
| 2002/0023654 A1 * | 2/2002 | Webb .......................... 128/899 |
| 2002/0089425 A1 | 7/2002 | Kubo et al. |
| 2002/0109600 A1 | 8/2002 | Mault et al. |
| 2002/0151810 A1 | 10/2002 | Wong et al. |
| 2003/0018430 A1 | 1/2003 | Ladetto et al. |
| 2003/0083596 A1 * | 5/2003 | Kramer et al. ............... 600/595 |
| 2003/0109258 A1 | 6/2003 | Mantyjarvi et al. |
| 2003/0139692 A1 * | 7/2003 | Barrey et al. ................. 600/595 |
| 2004/0225467 A1 | 11/2004 | Vock et al. |
| 2004/0236500 A1 | 11/2004 | Choi et al. |
| 2005/0033200 A1 | 2/2005 | Soehren et al. |
| 2005/0222801 A1 | 10/2005 | Wulff et al. |
| 2005/0232388 A1 | 10/2005 | Tsuji |
| 2005/0238132 A1 | 10/2005 | Tsuji |
| 2005/0240375 A1 | 10/2005 | Sugai |
| 2005/0248718 A1 | 11/2005 | Howell et al. |
| 2006/0100546 A1 * | 5/2006 | Silk ............................ 600/592 |
| 2006/0136173 A1 | 6/2006 | Case et al. |
| 2006/0223547 A1 | 10/2006 | Chin et al. |
| 2007/0063850 A1 | 3/2007 | Devaul et al. |
| 2007/0067094 A1 | 3/2007 | Park et al. |
| 2007/0082789 A1 * | 4/2007 | Nissila et al. ................. 482/8 |
| 2007/0130582 A1 | 6/2007 | Chang et al. |
| 2007/0142715 A1 * | 6/2007 | Banet et al. .................. 600/301 |
| 2009/0043531 A1 | 2/2009 | Kahn et al. |

OTHER PUBLICATIONS

Jones, L, et al., "Wireless Physiological Sensor System for Ambulatory Use", http://ieeexplore.ieee.org/xpl/freeabs_all.jsp?tp=&arnumber=1612917&isnumber=33861, Apr. 3-5, 2006.

Sinha, Alex, "Heart Monitoring Training", http://www.marathonguide.com/training/articles/HeartMonitorTraining.cfm, Apr. 4, 2007, 4 pages.

Heart Rate Monitors, http://www.suunto.com/suunto/Worlds/main/world_article_product no_ATL.jsp?CONTENT%3C%3Ecnt_id=10134198673968765&FOLDER%3C%3Efolder_id=9852723697225397&ASSORTMENT%3C%3East_id=1408474395903593&bmUID=1174532640618speed., Apr. 4, 2007, 1 page.

Dao, Ricardo, "Inclination Sensing with Thermal Accelerometers", MEMSIC, May 2002, 3 pages, http://www.memsic.com/data/pdfs/an-00mx-007.pdf.

Lee, Seon-Woo and Kenji Mase, "Recognition of Walking Behaviors for Pedestrian Navigation", IEEE International Conference on Control Applications, 2001, 5 pages.

Mizell, David, "Using Gravity to Estimate Accelerometer Orientation", Seventh IEEE International Symposium on Wearable Computers, 2003, 2 pages.

Weinberg, Harvey, "MEMS Motion Sensors Boost Handset Reliability", Jun. 2006, Feb. 21, 2007, 4 pages, http://www.mwrf.com/Articles/Print.cfm?ArticleID=12740.

DP Technologies, Inc. Office Action for U.S. Appl. No. 12/323,452 (P025C) mailed Jul. 31, 2009.

DP Technologies, Inc. Notice of Allowance for U.S. Appl. No. 11/603,472 (P025) mailed Oct. 10, 2008.

DP Technologies, Inc. Office Action for U.S. Appl. No. 11/603,472 (P025) mailed May 7, 2008.

Margaria, Rodolfo, "Biomechanics and Energetics of Muscular Exercise", Chapter 3, pp. 105-125, Oxford: Clarendon Press 1976.

DP Technologies, Inc. Office Action for U.S. Appl. No. 12/323,452 mailed Feb. 19, 2010.

Ormoneit, D., Sidenbladh, H., Black, M. J., & Hastie, T. (2000). Learning and tracking of cyclic human motion. Proceedings of NIPS 2000 (Neural Information Processing Systems), Denver, CO, 894-900.

* cited by examiner

CHEST STRAP HAVING HUMAN ACTIVITY MONITORING DEVICE

FIELD OF THE INVENTION

This invention relates to a method of monitoring human activity, and more particularly to a chest strap having a human activity monitoring device.

BACKGROUND

The development of Micro-Electro-Mechanical Systems (MEMS) technology has enabled manufacturers to produce inertial sensors (e.g., accelerometers) of sufficiently small size, cost, and power consumption to fit into portable electronic devices. Such inertial sensors can be found in a limited number of commercial electronic devices such as cellular phones, portable music players, pedometers, game controllers, and portable computers.

Step counting devices (e.g., pedometers) are used to monitor an individual's daily activity by keeping track of the number of steps that he or she takes. In general, step counting devices are clipped to a user's hip, and do not accurately count steps when placed elsewhere on a user's body.

Some step counting devices include an inertial sensor placed at specific locations on a user's body (e.g., in a user's shoe or belt). These inertial sensors wirelessly transmit raw acceleration data to a mobile device (e.g., a wrist watch) having an acceleration processing unit. The acceleration processing unit counts steps based on the received acceleration data. These steps can then be displayed on the mobile device.

BRIEF DESCRIPTION OF THE DRAWINGS

The present invention is illustrated by way of example, and not by way of limitation, and can be more fully understood with reference to the following detailed description when considered in connection with the following figures.

DETAILED DESCRIPTION

Embodiments of the present invention are designed to monitor human activity using an inertial sensor. In one embodiment, accelerations are monitored from an inertial sensor disposed in a chest strap. The accelerations are processed to determine one or more acceleration statistics, examples of which include speed, distance, and number of steps taken. The acceleration statistics are formatted to a generic format understandable by a plurality of devices. The formatted acceleration statistics are then transmitted. The transmission may be a wireless transmission to one or more of the plurality of devices.

Figure 1:
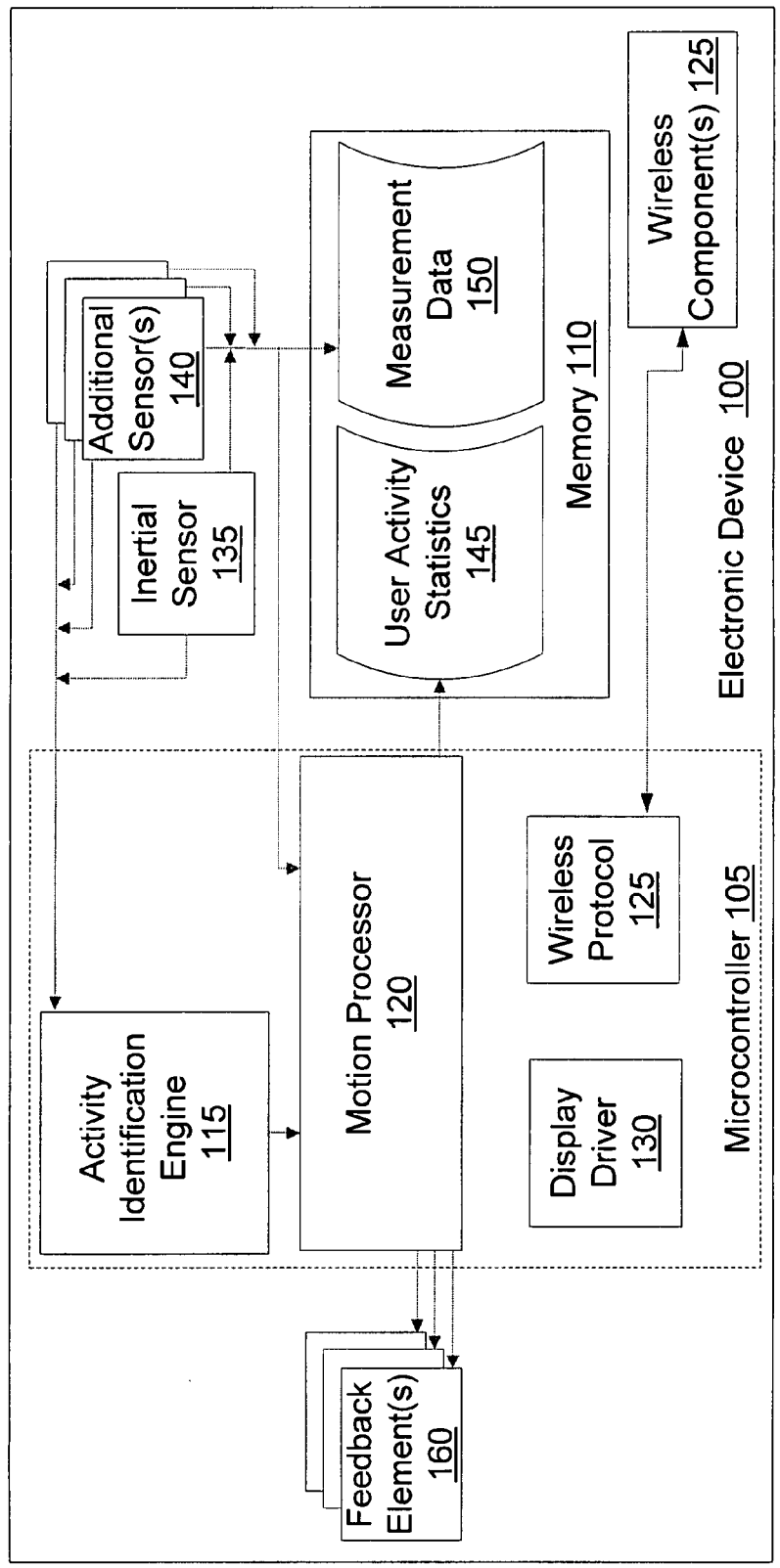
FIG. 1 is a block diagram illustrating an electronic device, in accordance with one embodiment of the present invention.

FIG. 1 is a block diagram illustrating an electronic device 100, in accordance with one embodiment of the present invention. In one embodiment, the electronic device 100 is a portable electronic device that includes one or more inertial sensors. The inertial sensors may measure accelerations along a single axis or multiple axes, and may measure linear as well as rotational (angular) accelerations. In one embodiment, one or more inertial sensors together provide three dimensional acceleration data.

The electronic device 100 may be used to identify user activities and count periodic human motions appropriate to the identified user activities. In one embodiment, electronic device 100 operates in conjunction with additional devices (e.g., a server or mobile computing device) and/or sensors to identify user activities and count periodic human motions. In one embodiment, periodic human motions may be accurately counted regardless of the placement and/or orientation of the device 100 on a user. Periodic human motions may be accurately counted whether the electronic device 100 maintains a fixed orientation or changes orientation during operation.

The electronic device 100 in one embodiment comprises an activity identification engine 115, a motion processor 120, an inertial sensor 135, a memory 110, a wireless protocol 125 and one or more wireless components 125. The electronic device 100 may further comprise one or more additional sensors 140 and a display driver 130.

The inertial sensor 135 may continuously take measurements of acceleration data. The measurements of acceleration data are taken at a sampling rate that may be fixed or variable. In one embodiment, the inertial sensor 135 receives a timing signal from a timer (not shown) in order to take measurements at the sampling rate. In one embodiment, the inertial sensor 135 is coupled to the activity identification engine 115 and to the motion processor 120, and acceleration measurement data is sent to the activity identification engine 115 and to the motion processor 120 for processing. In one embodiment, the inertial sensor 135 is coupled to the memory 110, and measurement data 150 from the inertial sensor 135 is stored in the memory 110.

In one embodiment, measurements are taken of the one or more additional sensors 140, and sent to the activity identification engine 115, the motion processor 120, and/or the memory 110. In one embodiment, the one or more additional sensors 140 include a heart rate sensor such as an electrocardiograph (EKG or ECG). Additional sensors 140 may also include additional inertial sensors, a pressure sensor, a moisture sensor, a capacitance sensor, a sound sensor (e.g., microphone), a heat sensor (e.g., thermometer, thermistor, etc.), or any other sensor capable of placement in a portable device. In one embodiment, the one or more additional sensors 140 take measurements at one or more set sampling rates that may be fixed or variable. In one embodiment, the set sampling rates are the same as the sampling rate at which the acceleration measurements are taken. Alternatively, one or more of the set sampling rates may vary from the sampling rate of the acceleration measurements.

In one embodiment, acceleration measurement data is processed by the activity identification engine 115 to identify a user activity. The activity identification engine 115 may identify the user activity from a plurality of identifiable user activities. The activity identification engine may identify a user activity by monitoring for different events, each event indicative of a different type of activity. In one embodiment, when enough events indicative of a particular user activity are detected, the activity identification engine 115 notifies the motion processor 120 that the identified activity is being performed by the user. One embodiment of a method for identifying user activities may be found in co-pending application U.S. Ser. No. 60/900,412, which is incorporated herein by reference. Alternative means of identifying user activities may be used in other embodiments.

In one embodiment, only acceleration measurement data is used to detect events that identify user activities. Alternatively, measurements from one or more of the additional sensors 140 may be used to facilitate user activity identification. For example, heart rate measurements showing a heart rate greater than a threshold value may indicate that a user is exerting himself, which may trigger an event for a user activity of, for example, running.

The motion processor 120 may process acceleration measurement data to detect periodic human motions. In one embodiment, a series of motion criteria are applied to the acceleration measurement data. If each of the motion criteria are satisfied, a periodic human motion may be identified, and counted. In one embodiment, a different set of motion criteria may apply for each user activity. Once the activity identification engine 115 has identified a user activity, the motion processor 120 may apply a set of motion criteria specific to the identified activity to detect appropriate periodic human motions. When an appropriate periodic human motion is detected, it may be recorded as one of the user activity statistics 145 (e.g., number of steps walked) in the memory 110. One embodiment of a method for counting periodic human motions may be found in co-pending application U.S. Ser. No. 11/644,455, which is incorporated herein by reference. Alternative means of counting periodic human motions may be used in other embodiments.

In one embodiment, the motion processor 120 generates user activity statistics based on measurements from the inertial sensor 135. Alternatively, one or more of the additional sensors 140 may also be used to generate user activity statistics. Examples of user activity statistics include periodic human motion counts, distance, speed, etc. In one embodiment, the user activity statistics are formatted by the motion processor 120 once they are generated. The user activity statistics may be formatted into one or more formats. In one embodiment, the user activity statistics are formatted to a generic format understandable by multiple different computing devices. Examples of generic formats for the user activity statistics include extensible markup language (XML) and standard generalized markup language (SGML). In one embodiment, the format used for the user activity statistics is user selectable.

One type of user activity statistic is a periodic human motion count. A separate periodic human motion count may be maintained for each type of periodic human motion. For example, a separate count may be maintained for walking, running, inline skating, rowing, bicycling, and so on. A total periodic human motion count that includes all periodic human motions may also be maintained.

Other user activity statistics include heart rate, body temperature, breathing rate, distance, speed, altitude change, and so on. These user activity statistics may be correlated to specific user activities. Therefore, a user may find out, for example, the distance run versus the distance walked during a training session, as well as average speed, average running heart rate, average walking heart rate, and so on. A user may also determine, for example, daily activity levels, weekly activity levels, etc., from the user activity statistics. This may provide a user with information useful for athletic training and health.

In one embodiment, electronic device 100 includes one or more feedback elements 160. Feedback elements 160 may be part of the electronic device 100, or may be external to the electronic device. Feedback elements 160 may provide one or more of aural feedback (e.g, a buzz, beep, tune, spoken words, etc.), visual feedback (e.g., a blinking or solid light, number display, etc.) and tactile feedback (e.g., a vibration, movement, or slight shock). Feedback may be used, for example, to notify a user to speed up or to slow down, to notify a user that a specified period of time has elapsed, etc. In one embodiment, the type of user feedback, and when to provide user feedback, is user selectable. For example, a user may select to be given a notice to slow down when the user's heart rate exceeds an upper threshold, and to speed up when the user's heart rate falls below a lower threshold. Multiple feedback conditions may be active concurrently. For example, a user may select to receive feedback if a running speed falls below a lower threshold and if a heart rate falls below a lower threshold. Thereby, a user may more accurately control workout intensity.

In one embodiment, user activity statistics 145 are stored in memory 110. Alternatively, the user activity statistics may be transmitted to an additional electronic device (not shown) such as a server or storage unit. In one embodiment, the memory 110 stores measurement data 150, which may later be processed by the electronic device 100, or by an external device such as a server. Alternatively, measurement data 150 may not be stored, or it may be transmitted to an additional electronic device for storage.

In one embodiment, the electronic device 100 includes a wireless protocol 125 and one or more wireless components 125. The wireless protocol may be Bluetooth, Zigbee, infrared, radiofrequency (RF), personal area network (PAN), or any other wireless communication protocol. Alternatively, the electronic device 100 may include a wired protocol such as firewire, universal serial bus (USB), etc. In one embodiment, the electronic device 100 includes both a wireless protocol 125 and a wired protocol. The wireless and/or wired protocol may enable the electronic device to communicate with additional devices, such as a server, mobile device, personal computer, etc.

In one embodiment, the electronic device 100 includes a display driver 130. The display driver 130 may control a built in display (not shown) of the electronic device, or an external display (not shown) that may be connected to the electronic device 100.

In one embodiment, the activity identification engine 115, motion processor 120, display driver 130 and wireless protocol 125 are logics executed by a microcontroller 105, field programmable gate array (FPGA), application specific integrated circuit (ASIC), or other dedicated processing unit. In another embodiment, one or more of the activity identification engine 115, motion processor 120, display driver 130 and wireless protocol 125 may be logics executed by a central processing unit. Alternatively, one or more of the activity identification engine 115, motion processor 120, display driver 130 and wireless protocol 125 may include a state machine (e.g., an internal logic that knows how to perform a sequence of operations), a logic circuit (e.g., a logic that goes through a sequence of events in time, or a logic whose output changes immediately upon a changed input), or a combination of a state machine and a logic circuit.

Figure 2:
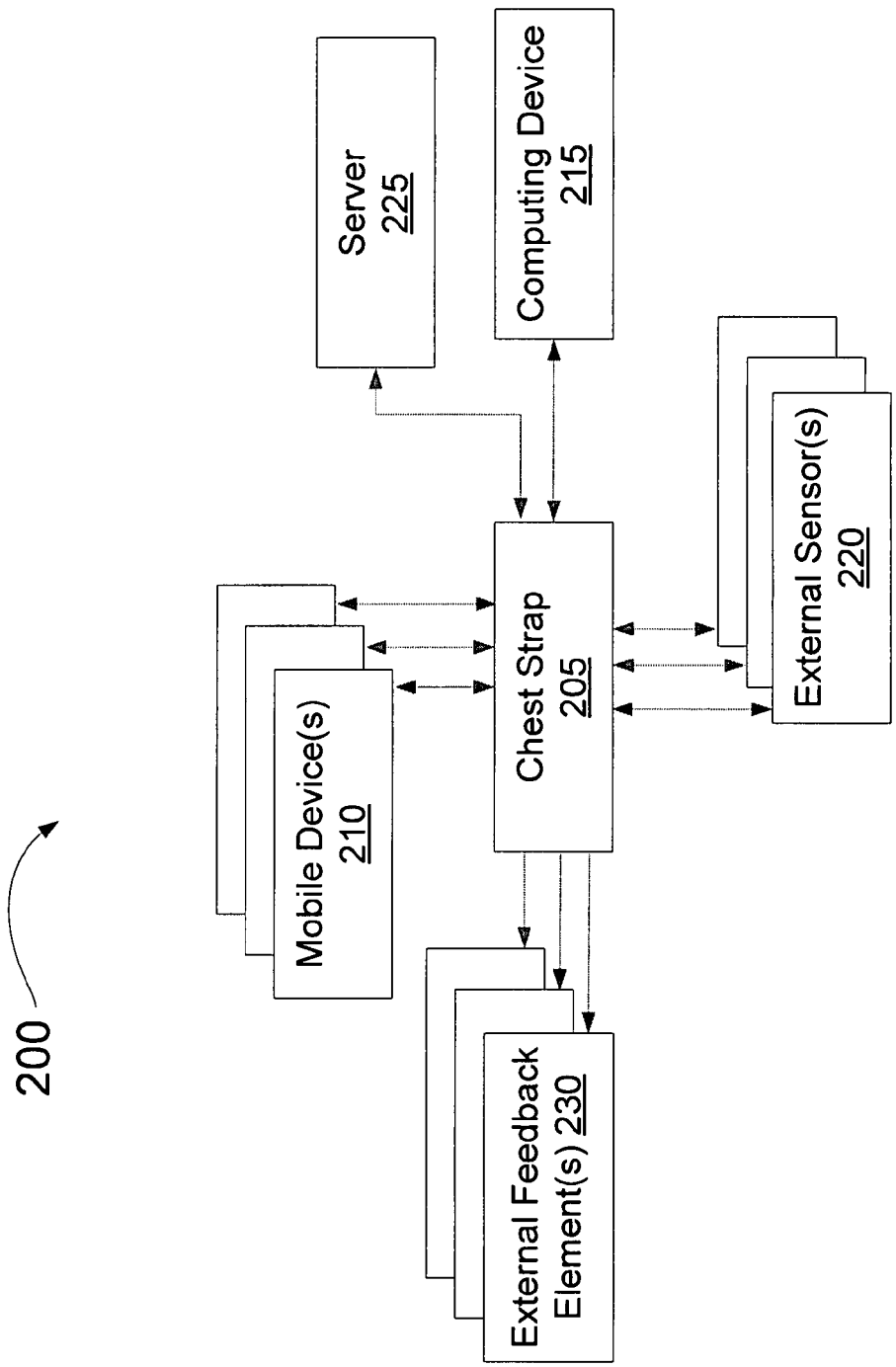
FIG. 2 is a block diagram illustrating a motion identification system, in accordance with one embodiment of the present invention.

FIG. 2 is a block diagram illustrating a motion identification system 200, in accordance with one embodiment of the present invention. The motion identification system 200 in one embodiment includes a chest strap 205 wirelessly connected to one or more mobile devices 201, one or more external sensors 220, one or more external feedback elements 230, a computing device 215, and a server 225. In alternative embodiments, the chest strap 205 may be connected to only some of the mobile devices 210, external sensors 220, server 225 and computing device 215. In one embodiment, the chest strap 205 is not connected to any devices or sensors. In one embodiment, the chest strap 205 includes electronic device 100 of FIG. 1. In one embodiment, chest strap 205 is a strap worn under or over clothing. Alternatively, chest strap 205 may be attached to a garment. Alternatively, the chest strap 205 may be a garment made of materials incorporating sensors, processors, and/or other components.

Returning to FIG. 2, the distribution of the functionality between the chest strap 205 and the devices, sensors and server may vary. In one embodiment, all sensor data is processed by the chest strap 205. The sensor data may be formatted by the chest strap 205 into a generic format understandable by one or more of the mobile devices 210, server 225 and computing device 215. Alternatively, the chest strap 205 may transmit unprocessed and/or unformatted data to one or more of the mobile devices 210, server 225, and/or computing device 215. In one embodiment, signals are sent to external feedback elements 230 to provide user feedback, for example, to indicate that user should speed up or slow down.

Figure 3:
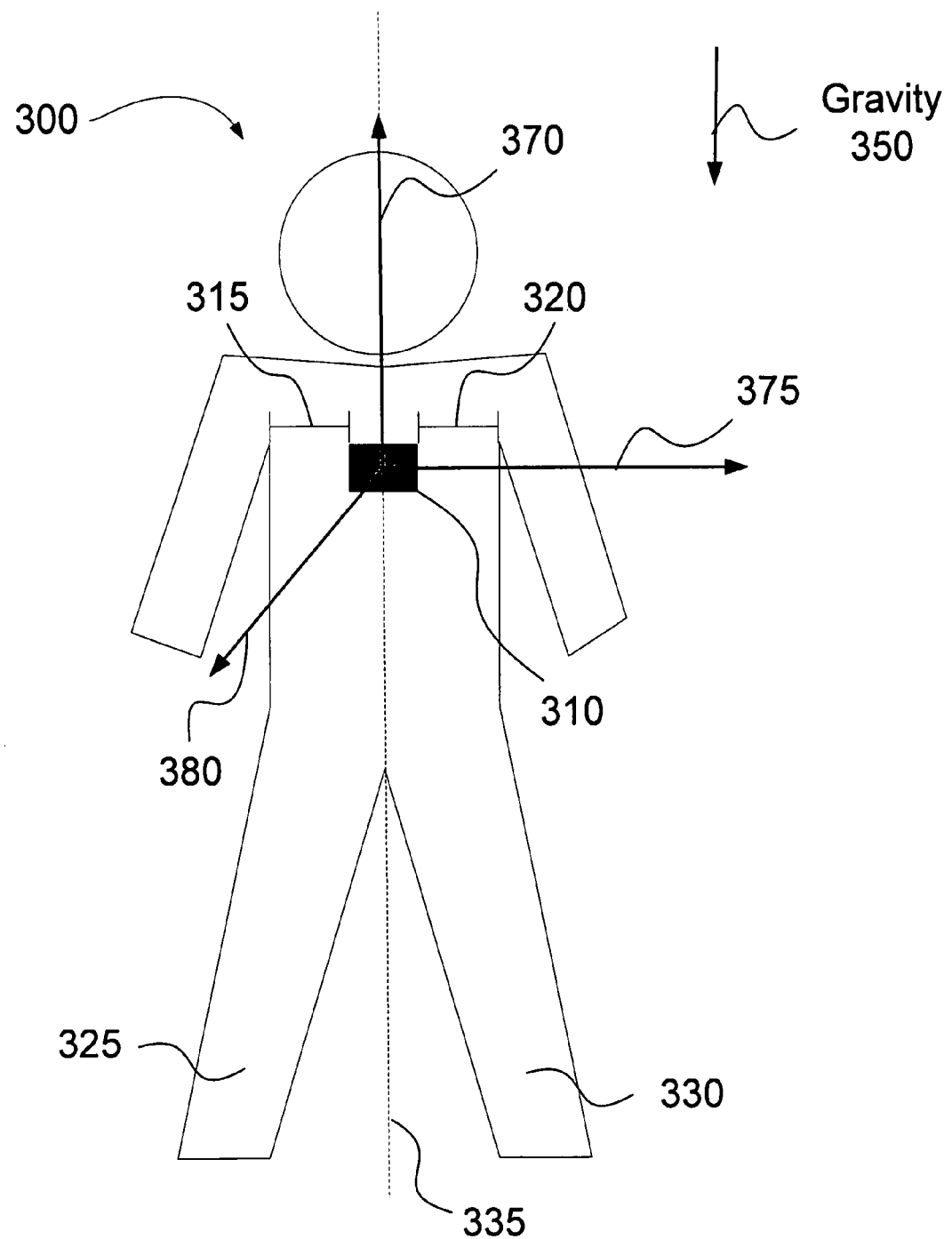
FIG. 3 illustrates a front view of a user wearing a chest strap, in accordance with one embodiment of the present invention.

FIG. 3 illustrates a front view of a user 300 wearing a chest strap, in accordance with one embodiment of the present invention. In one embodiment, the chest strap is chest strap 205 of FIG. 2.

Referring to FIG. 3, user 300 has an axis of symmetry 335 that divides user's 300 body into a right half 325 and a left half 330. In one embodiment, the chest strap 310 is disposed on the user's 300 chest such that a center of the chest strap 310 approximately lines up with axis of symmetry 335. Therefore, the chest strap 310 may be equidistant from a right side of the torso 315 and from a left side of the torso 320. Alternatively, the chest strap 310 may be disposed approximately along the line of symmetry 335 at other locations of user's 300 body, such as at a user's 300 waist or back.

Placement of chest strap 310 along the line of symmetry 335 in one embodiment enables differentiation between accelerations caused by motions from the right half 325 of user's body and left half 330 of user's body. Therefore, chest strap 310 may distinguish between, for example, steps taken by a right leg and steps taken by a left leg. This may assist users in refining their running technique, or provide an indication that something may be wrong with a user's left or right leg.

In one embodiment, the chest strap 310 is disposed on user's 300 chest at a fixed orientation such that a first axis 370 of the chest strap is approximately aligned to gravity 350 when user 300 is standing. In one embodiment, a second axis 375 of the chest strap extends laterally to user 300 (Medial-Lateral Axis), and a third axis 380 of the chest strap extends front-to-back in relation to user's 300 body (Ventral-Dorsal Axis).

In one embodiment, placement of the chest strap 310 on user's 300 chest enables measurement of the center of mass of user 300. Such placement reduces random and/or secondary motions caused by, for example, arm movement or head movement. This may enable clean acceleration measurements to be taken along the first axis, which may improve the accuracy of user activity statistics.

In one embodiment, the fixed orientation of the chest strap 310 enables identification of vertical movement, lateral movement, and front-to-back movement. In one embodiment, the fixed orientation of the chest strap 310 further enables first axis 370 to be used for counting periodic human motions without first determining a dominant axis (e.g., an axis aligned closest to gravity). Alternatively, the dominant axis may be determined before or in conjunction with counting periodic human motions. One embodiment of a method for determining a dominant axis may be found in co-pending application U.S. Ser. No. 11/603,472, which is incorporated herein by reference. Other means of determining a dominant axis may be used in other embodiments. A more detailed discussion of determining a dominant axis is discussed below with reference to FIGS. 7-13.

In one embodiment, the dominant axis may be used to indicate whether a user has properly donned chest strap 310. For example, the dominant axis may be compared to the first axis 370, second axis 375 and third axis 380 to determine whether chest strap 310 is properly oriented on user's 300 torso.

A combination of the fixed orientation of the chest strap 310 and the dominant axis may be used to determine user 300 body position. In one embodiment, the chest strap 310 may identify whether a user 300 is prone or upright. In one embodiment, the chest strap 310 can further identify a degree of inclination for the user 300 (e.g., degree to which user 300 is leaning forward or backward).

Figure 4:
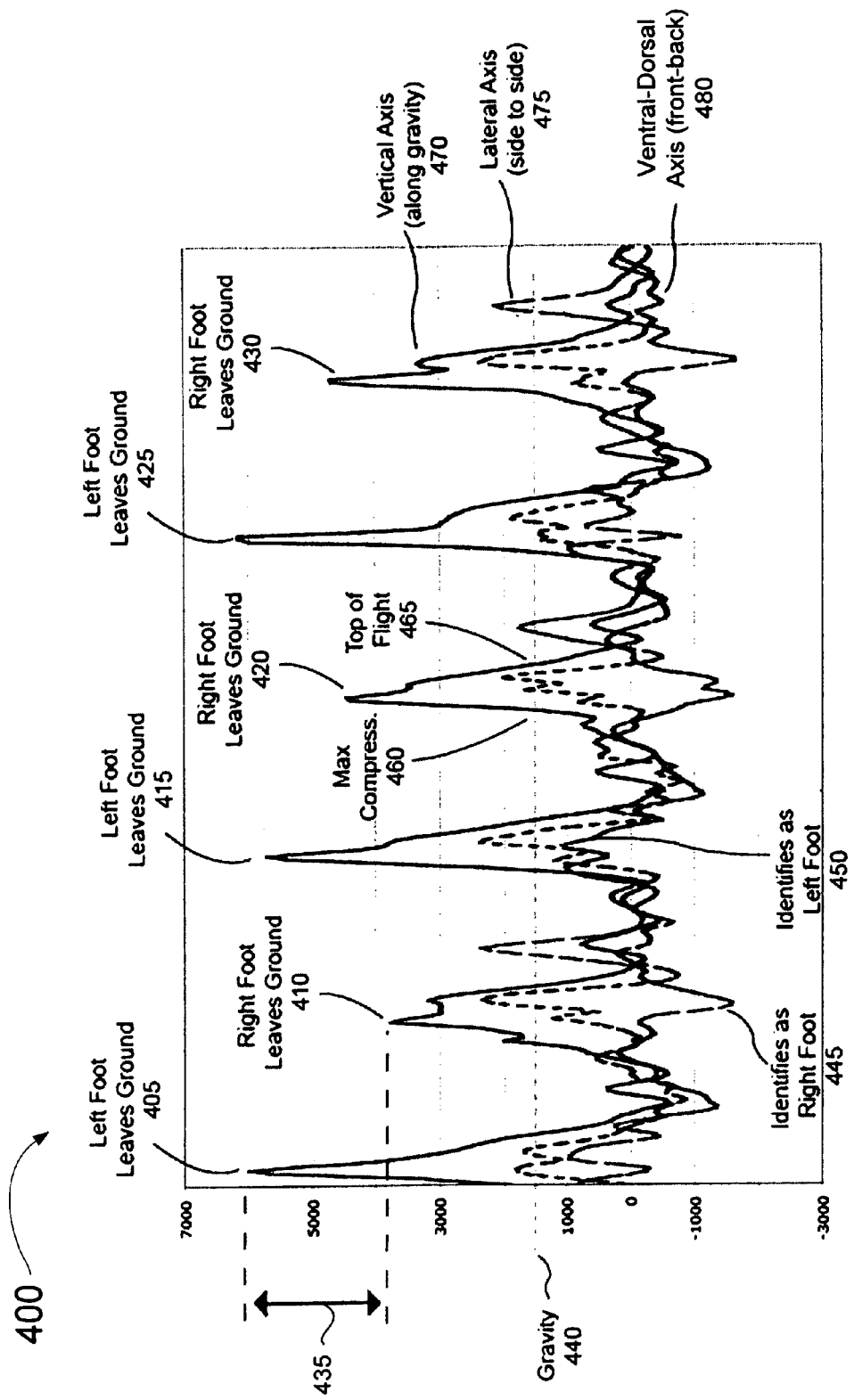
FIG. 4 illustrates a first exemplary motion cycle graph that shows a user engaged in a user activity as measured by an accelerometer located in a chest strap.

FIG. 4 illustrates a first exemplary motion-cycle graph 400 that shows a user engaged in a user activity as measured by an accelerometer located in a chest strap. In one embodiment, the chest strap is chest strap 310 of FIG. 3, and is approximately aligned to axis of symmetry 335 of FIG. 3 in a fixed orientation.

Referring to FIG. 4, the exemplary motion-cycle graph 400 shows acceleration data taken with a single tri-axis inertial sensor. The acceleration at a given period of time is represented for a vertical axis 470, a lateral axis 475, and a ventral-dorsal axis 480.

In one embodiment, the vertical axis 470 is used to identify steps. In one embodiment, gravity 440 provides a constant acceleration along the positive direction of the vertical axis 470. Accordingly, any positive acceleration along the vertical axis 470 is acceleration towards the earth, and any negative acceleration along the vertical axis 470 is acceleration away from the earth. Thus, a foot leaving the ground is indicated by a peak (spike) of acceleration along the vertical axis 470. Such peaks of acceleration are shown for the left foot 405, 415, 425 and for the right foot 410, 420, 430. In alternative embodiments, gravity may provide a permanent acceleration along the negative direction of the vertical axis 470. In such an embodiment, valleys (spikes) along the vertical axis 470 would indicate a foot leaving the ground.

Accelerations along the vertical axis 470 may be used to determine multiple different user activity statistics. In one embodiment, the vertical axis may be used to identify a magnitude of acceleration that each leg experiences. This may be useful, for example, to determine how much strain is placed on each leg during running and/or walking. In one embodiment, points at which vertical acceleration 470 crosses 465 gravity 440 (where the accelerations equal gravity) indicate that a user is in a state of free fall. In one embodiment, a shape of the peak (spike) of acceleration measurements along the vertical axis 470 indicates an elasticity of the surface being walked or run on. For example, a sharp spike indicates a surface with relatively low elasticity (e.g., concrete), while a gradual spike indicates a surface with relatively high elasticity (e.g., a rubber track). Surfaces with a greater elasticity absorb a greater amount of user impact, and are therefore less damaging to a user's body. Other useful data may also be determined from the vertical axis 470.

In one embodiment, lateral axis 475 is used to identify whether a step is being taken by a right foot or by a left foot. In the illustrated embodiment, any negative acceleration along the lateral axis indicates acceleration towards the right, and any positive acceleration along the lateral axis indicates acceleration towards the left. Thus, the lateral axis 475 may identify accelerations caused by the right foot 445 and accelerations caused by the left foot 450. In alternative embodiments, a positive acceleration may indicate acceleration to the right, and a negative acceleration may indicate acceleration to the left.

In one embodiment, additional specifics about a user's gait may be determined based on accelerations along the lateral axis 475, the ventral-dorsal axis 480 and/or the vertical axis 470. For example, the illustrated embodiment shows a greater acceleration along the vertical axis 470 from the left foot than from the right foot. This difference between acceleration peaks 435 along the vertical axis 470 may identify a problem with the right leg (e.g., an injury or potential injury). Other useful information about a user's gait may also be determined, such as an amount of lateral motion accompanying each step, an amount of unnecessary vertical motion with each step, an amount of force exerted by each step, etc.

Though FIG. 4 has been described in the context of identifying steps for walking and running, the techniques described with reference to FIG. 4 may equally be used when counting other periodic human motions associated with other user activities. Examples of such additional user activities include inline skating, swimming, rowing, etc.

Figure 5:
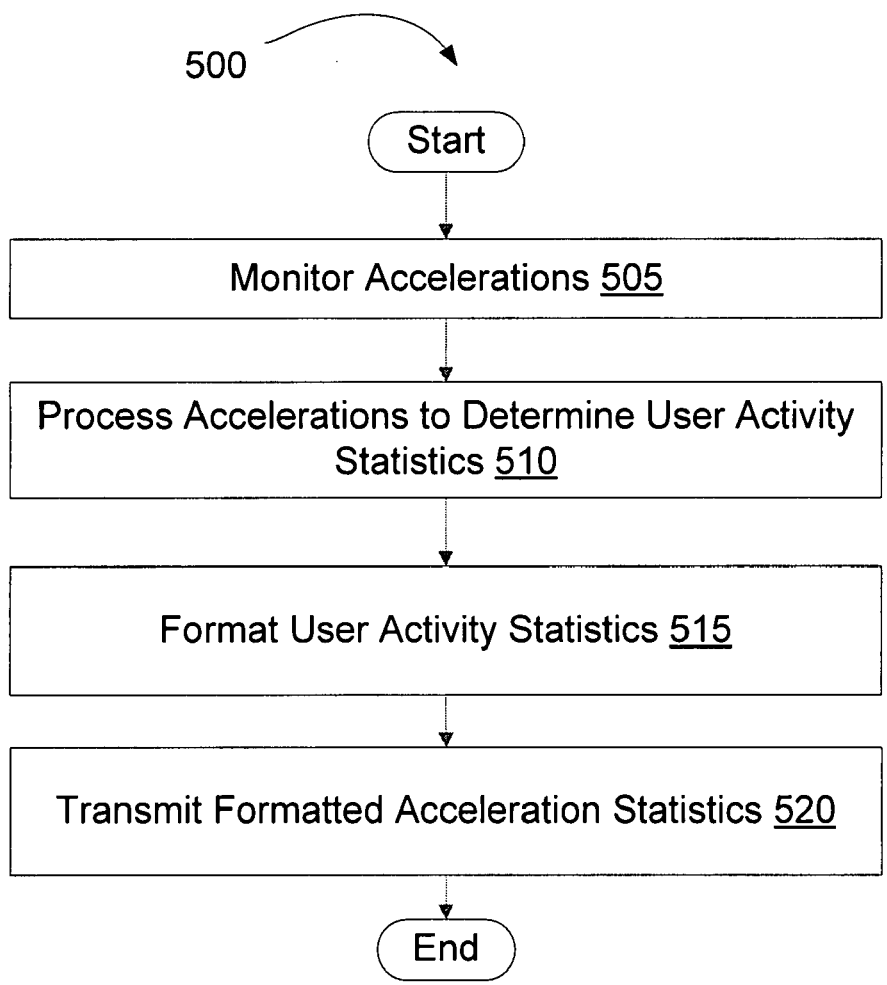
FIG. 5 illustrates a flow diagram for a method of monitoring human activity using an inertial sensor, in accordance with one embodiment of the present invention.

FIG. 5 illustrates a flow diagram for a method 500 of monitoring human activity using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 500 is performed by the electronic device 100 of FIG. 1. In one embodiment, method 500 is performed by the motion identification system 200 of FIG. 2.

Referring to FIG. 5, method 500 begins with monitoring accelerations (block 505). Accelerations may be monitored with an inertial sensor, or other acceleration monitoring device. At block 510, the accelerations are processed to determine user activity statistics. Examples of user activity statistics include number of periodic human motions counted, user speed, distance traveled, heart rate, and so on. For some user activity statistics such as heart rate, measurements are gathered from additional sensors (e.g., an ECG). At block 515, the user activity statistics are formatted. In one embodiment, the user activity statistics are formatted into a generic format understandable by multiple different computing devices. Examples of a generic format include XML and SGML. In one embodiment, the "generic" format may be selected by the user. In one embodiment, the generic format includes formats such as spreadsheet formats, comma-delimited formats, human readable formats, etc. At block 520, the formatted user activity statistics are transmitted. In one embodiment, the formatted user activity statistics are transmitted to a mobile device such as a mobile phone, personal digital assistant (PDA), laptop computer, wrist watch, etc. Alternatively, the formatted user activity statistics may be transmitted to a server and/or a computing device such as a personal computer.

Figure 6:
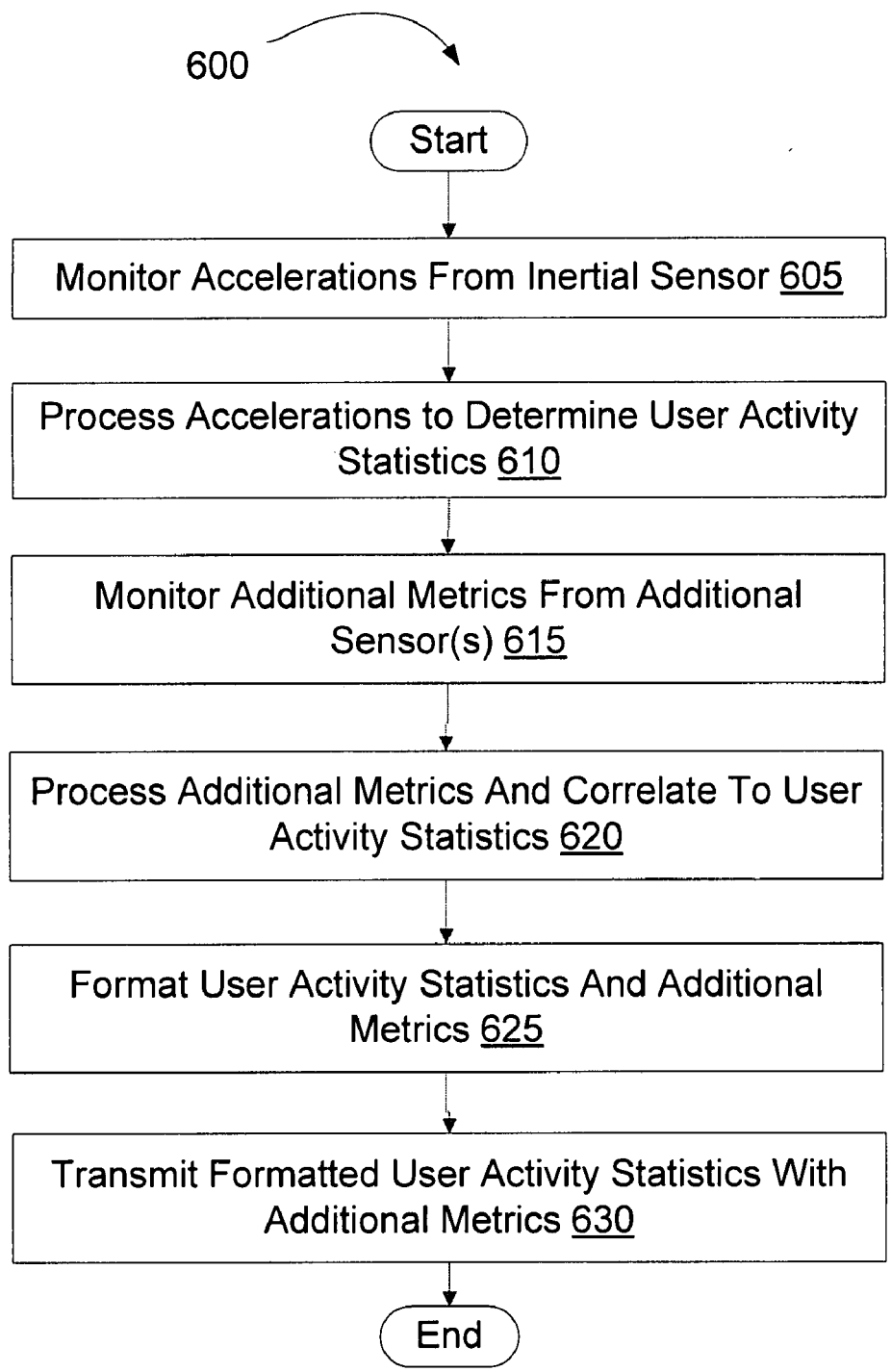
FIG. 6 illustrates a flow diagram for a method of monitoring human activity using an inertial sensor, in accordance with one embodiment of the present invention.

FIG. 6 illustrates a flow diagram for a method 600 of monitoring human activity using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 600 is performed by the electronic device 100 of FIG. 1. In one embodiment, method 600 is performed by the motion identification system 200 of FIG. 2.

Referring to FIG. 6, method 600 begins with monitoring accelerations (block 605). Accelerations may be monitored with an inertial sensor, or other acceleration monitoring device. At block 610, the accelerations are processed to determine user activity statistics. At block 615, additional metrics are monitored from one or more additional sensors. Examples of additional sensors include a heat sensor, a pressure sensor, a heart rate sensor, etc. Examples of additional metrics include heart rate, body temperature, altitude, etc.

At block 620, the additional metrics are processed and correlated to the user activity statistics. At block 625, the user activity statistics and the additional metrics are formatted. In one embodiment, the user activity statistics are formatted into a generic format understandable by multiple different computing devices. At block 630, the formatted user activity statistics are transmitted along with the additional metrics. In one embodiment, the formatted user activity statistics and additional metrics are transmitted to a mobile device such as a mobile phone, personal digital assistant (PDA), laptop computer, wrist watch, etc. Alternatively, the formatted user activity statistics may be transmitted to a server and/or a computing device such as a personal computer.

Figure 7:
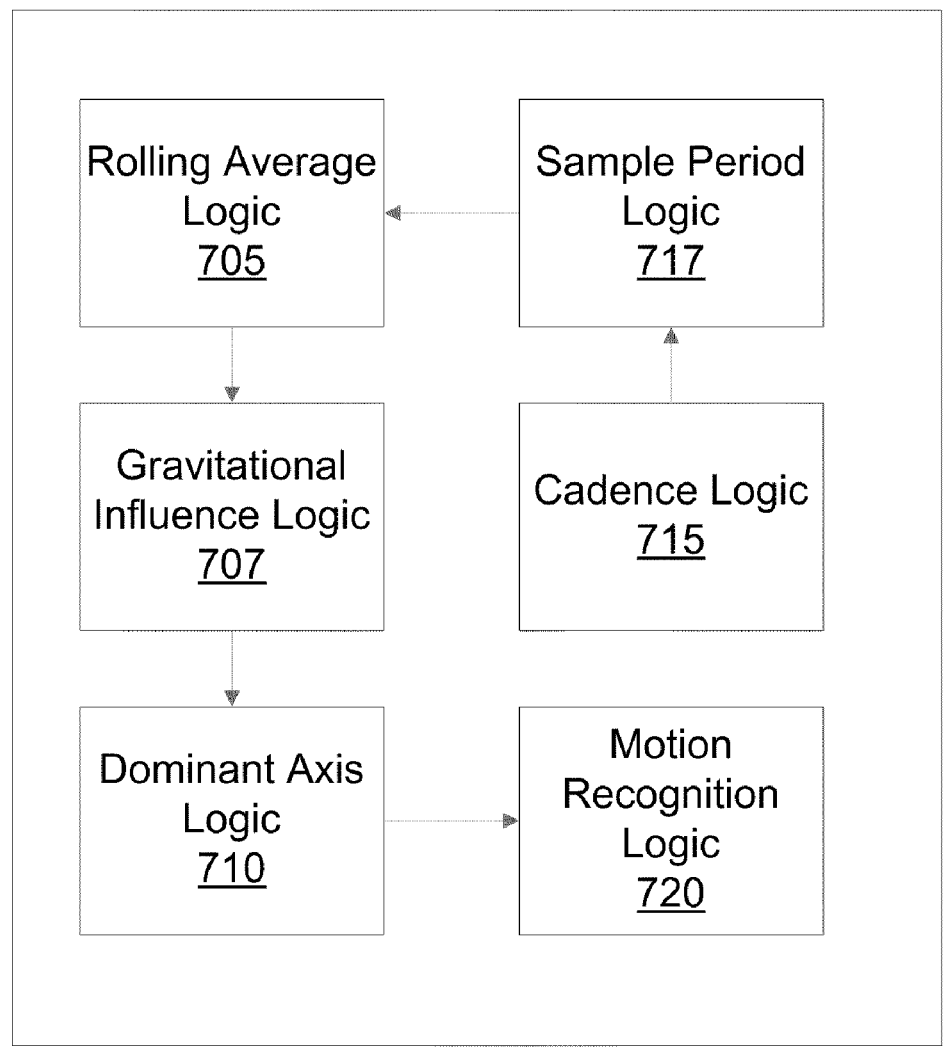
FIG. 7 is a block diagram illustrating one embodiment of an electronic device.

FIGS. 7-13 illustrate embodiments of methods and devices for determining a dominant axis. Referring to FIG. 7, a block diagram illustrating an electronic device 701 is shown in accordance with one embodiment of the present invention. The electronic device 701 comprises a rolling average logic 705, a gravitational influence logic 707, a dominant axis logic 710, a cadence logic 715, a sample period logic 717, and a motion recognition logic 720. In one embodiment, the electronic device 701 is a portable electronic device that includes an accelerometer.

The rolling average logic 705 creates one or more rolling averages of accelerations as measured by an accelerometer over a sample period. In one embodiment, the rolling average logic 705 creates a rolling average of accelerations along a single axis. In another embodiment, the rolling average logic 705 creates rolling averages of accelerations along multiple axes. The length of the sample period over which the rolling average is taken determines the amount of past acceleration data that is averaged with present acceleration data. In a longer sample period, more past acceleration data is stored.

The rolling average logic 705 can create a simple rolling average and/or an exponential rolling average. In a simple rolling average, all data is treated equally. In an exponential rolling average, the most recent data is given more weight. In one embodiment, the rolling average logic 705 creates a rolling average for each of the axes along which acceleration data is taken.

In one embodiment, the cadence logic 715 detects a period of a cadence of motion based upon user activity, and the sample period logic 717 sets the sample period of the rolling averages based on the period of the cadence of motion. In one embodiment the gravitational influence logic 707 identifies a gravitational influence based upon the rolling averages of accelerations. The dominant axis logic 710 assigns the dominant axis based upon the gravitational influence. The motion recognition logic 720 can use the dominant axis to facilitate motion recognition.

Figure 8A:
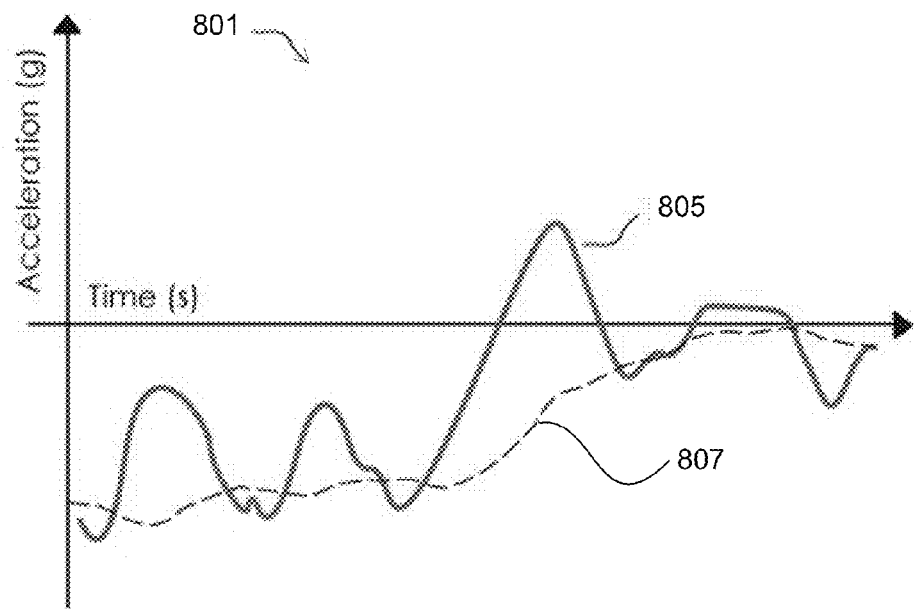
FIGS. 8A and 8B illustrate exemplary rolling average graphs that measure time versus acceleration.
Figure 8B:
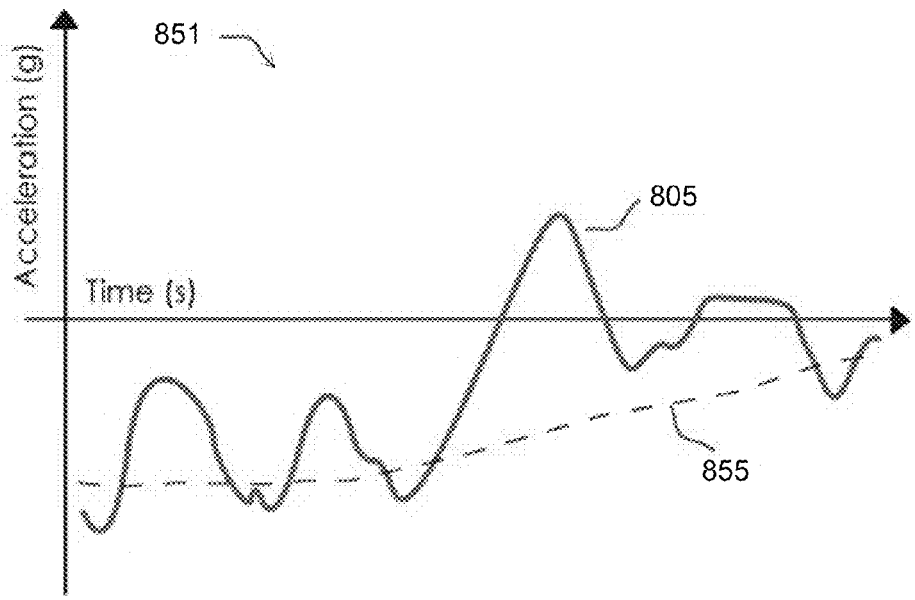

FIGS. 8A and 8B illustrate an exemplary first rolling average graph 801 and second rolling average graph 851, respectively. Both graphs represent time versus acceleration, shown by line 805. The first rolling average graph 801 shows a first rolling average 807 based on a relatively short sample period. The second rolling average graph 851 shows a second rolling average 855 based on a longer sample period. The length of the sample period determines how sensitive the rolling average is to fluctuations in acceleration. A short sample period as shown in FIG. 8B will measure brief fluctuations. In a longer sample period, as shown in FIG. 8A, brief fluctuations are averaged out. Additionally, a rolling average always lags behind the present acceleration, and a longer sample period causes greater lag. Comparing FIGS. 8A and 8B, it can be seen that the second rolling average 855 requires more time than the first rolling average 807 to reflect a change in acceleration.

In one embodiment, the sample period is preconfigured. In one embodiment, the size of the sample period is adjusted based on the application(s) using the accelerometer data. In one embodiment, the sample period can be user selected from a list of options. In one embodiment, the sample period can be determined by the cadence logic 705 and the sample period logic 718.

In one embodiment, two or more rolling averages of accelerations are tracked concurrently. The two or more rolling averages can be rolling averages along the same or different axes. In one embodiment, two or more rolling averages are tracked concurrently for each of the axes. Concurrent tracking of rolling averages can be beneficial where a user is performing two actions at the same time, each of which requires a different level of sensitivity for acceleration measurements. For example, the use of different sample periods for two rolling averages can be useful where the electronic device 701 is simultaneously counting steps and tracking motions of a user as called for by a motion sensitive game. In such an example, the motion sensitive game might require a very short sample period to measure quick motions, while the step counter might require a longer sample period so as to register only the user's steps.

Returning to FIG. 7, in one embodiment the cadence logic 715 detects a period of a cadence of motion based upon user activity (e.g. rollerblading, biking, running, walking, etc). Many types of motions that are useful to keep track of have a periodic set of movements. Specific periodic human motions may be characteristic of different types of user activity. For example, to walk, an individual must lift a first leg, move it forward, plant it, then repeat the same series of motions with a second leg. In contrast, a person rollerblading performs a repeated sequence of pushing, coasting, and lift-off for each leg. For a particular individual, the series of walking motions will usually occur in the same amount of time, and the series of rollerblading motions will usually occur in about the same amount of time. The repeated set of motions defines the cadence of the motion, while the amount of time over which the series of motions occurs defines the period of the cadence of the motion. For simplicity, the term "step" is used in the following description to describe the user activity being evaluated. However, in the context of this application, the term "step" should be taken to mean any user activity having a periodic set of movements.

Figure 9:
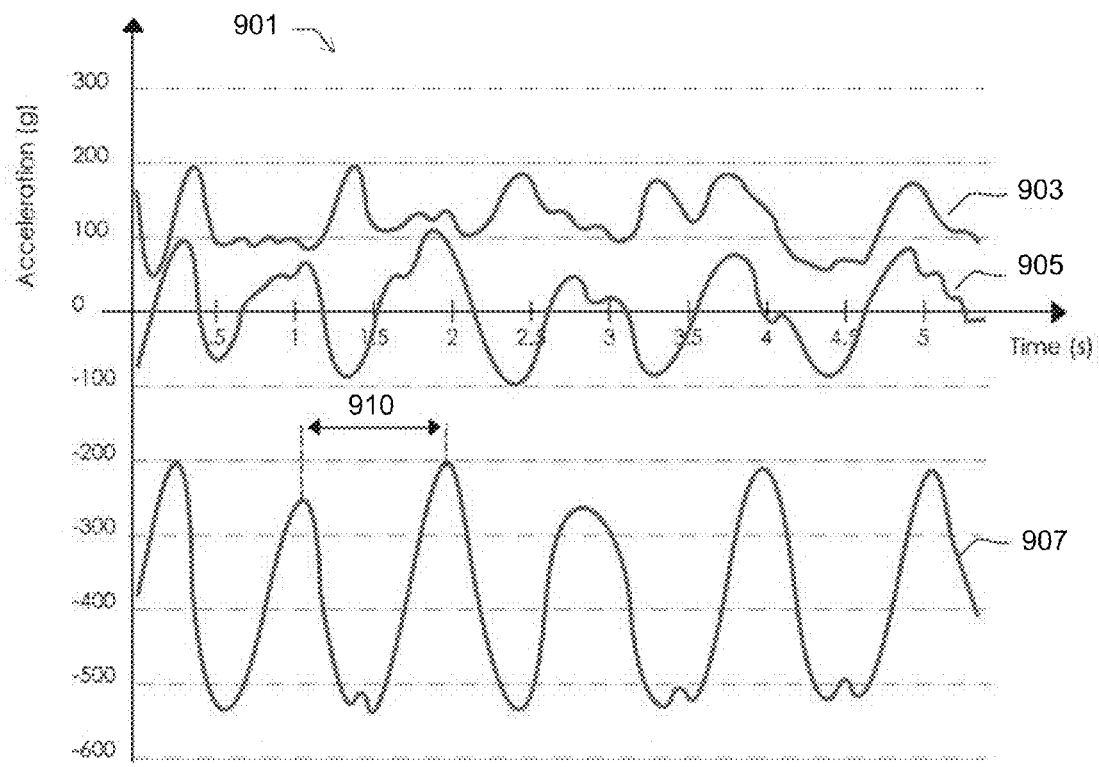
FIG. 9 illustrates an exemplary cadence of motion graph that measures time versus acceleration.

FIG. 9 illustrates a cadence of motion graph 901 that measures time versus acceleration. The acceleration at a given period of time is represented for a first axis 903, a second axis 905, and a third axis 907. In one embodiment, a cadence logic analyzes the acceleration along the first axis 903, second axis 905 and third axis 907 to detect a pattern. Once a pattern is detected, a period of the pattern is determined. This period corresponds to the period of the cadence of motion. FIG. 9 shows a period of a cadence of motion 910 for the third axis 907. The same period can also be seen to a lesser degree in the second axis 905 and the first axis 903.

In one embodiment, periods can be determined for multiple cadences of motion. For example, if a user simultaneously walks and tosses a ball in the air, in one embodiment the system can detect a period of the cadence of tossing the ball, and a period of the cadence of walking.

Returning back to FIG. 7, once the period of a cadence of motion is detected, the sample period logic 717 can set the sample period of the rolling average based upon the period of the cadence of motion. In one embodiment, the sample period is set such that it is approximately the length of the period of the cadence of motion. Alternatively, the sample period can be set so that it exceeds the length of the period of the cadence of motion. In one embodiment, the sample period is set such that it is a multiple of the period of the cadence of motion.

In one embodiment, the gravitational influence logic 707 identifies a gravitational influence based upon the rolling average or averages of accelerations. An accelerometer measures both dynamic accelerations, caused by user movement, and static acceleration, caused by gravity. This static acceleration is measured by an accelerometer as a constant acceleration that is equal and opposite to the force of gravity. Over a period of a cadence of motion, the dynamic acceleration caused by user activity tends to average towards zero, which leaves primarily the static acceleration. The axis with the largest absolute rolling average is the axis most influenced by gravity.

The axis that is most influenced by gravity can change over time. For example, as an electronic device 701 is rotated, the influence of gravity will change for at least two axes in a three axis accelerometer. At some point in the rotation, the axis that experiences the most gravitational influence will change. This change is shown in FIGS. 10A and 10B.

Figure 10A:
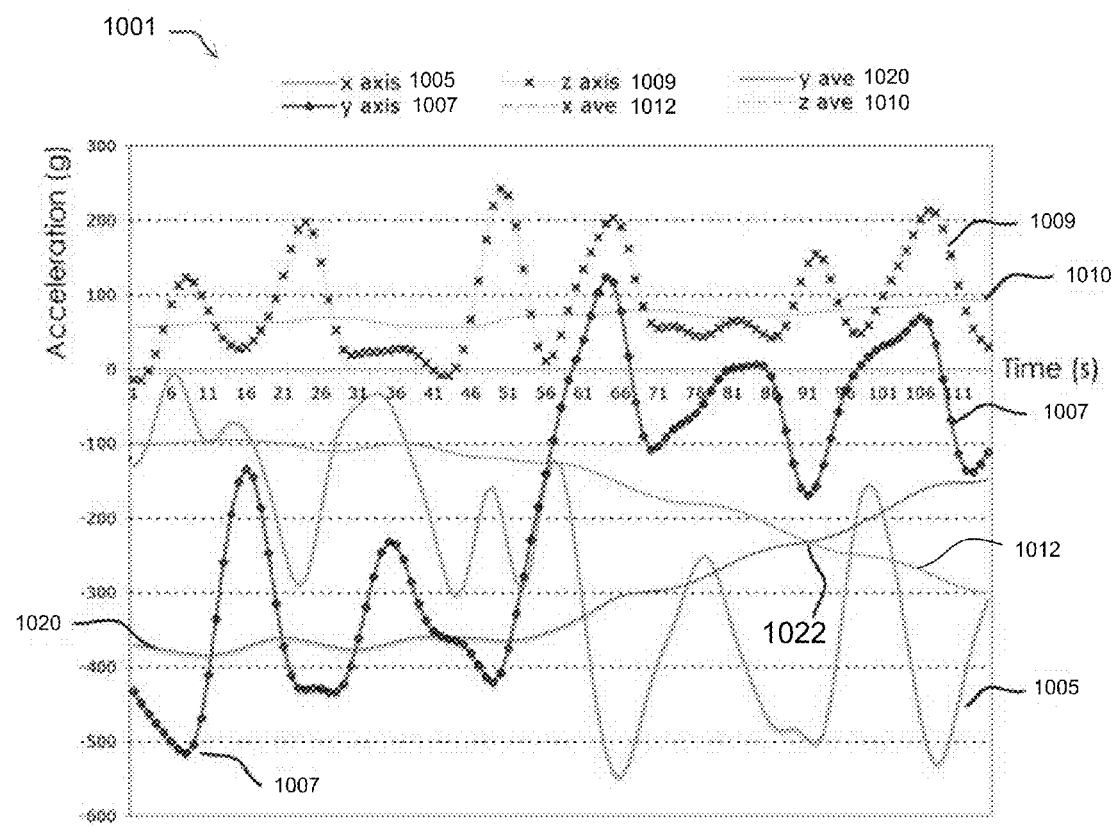
FIGS. 10A and 10B illustrate exemplary gravitational influence graphs.

FIG. 10A illustrates a first gravitational influence graph 1001 for a data set over a rolling average sample period of 2.5 seconds. Accelerations are shown along an x-axis 1005, a y-axis 1007, and a z-axis 1009. In FIG. 10A, a device being measured is rotated about the z-axis over time. At time T=0, the y-axis 1007 has the largest absolute acceleration value at over −400, while at time T=111 the x-axis has the largest absolute acceleration value at −300.

In FIG. 10A, a first x-axis rolling average 1012, a first y-axis rolling average 1020 and a first z-axis rolling average 1010 are shown. The axis with the largest absolute rolling average is the axis that is most influenced by gravity at a given time. As rotation occurs, the rolling averages change to reflect a change in the gravitational influence on the device. Initially, the x-axis 1005 is most influenced by gravity. At the first point of intersection 1022 of the first x-axis rolling average 1012 and the first y-axis rolling average 1020, the y-axis 1007 becomes the axis most influenced by gravity. However, the axis that experiences the greatest gravitational influence changes at a time after the rotation has actually occurred. This is due to a lag caused by the 2.5 second sample period. To reduce this lag, the sample period can be reduced.

Figure 10B:
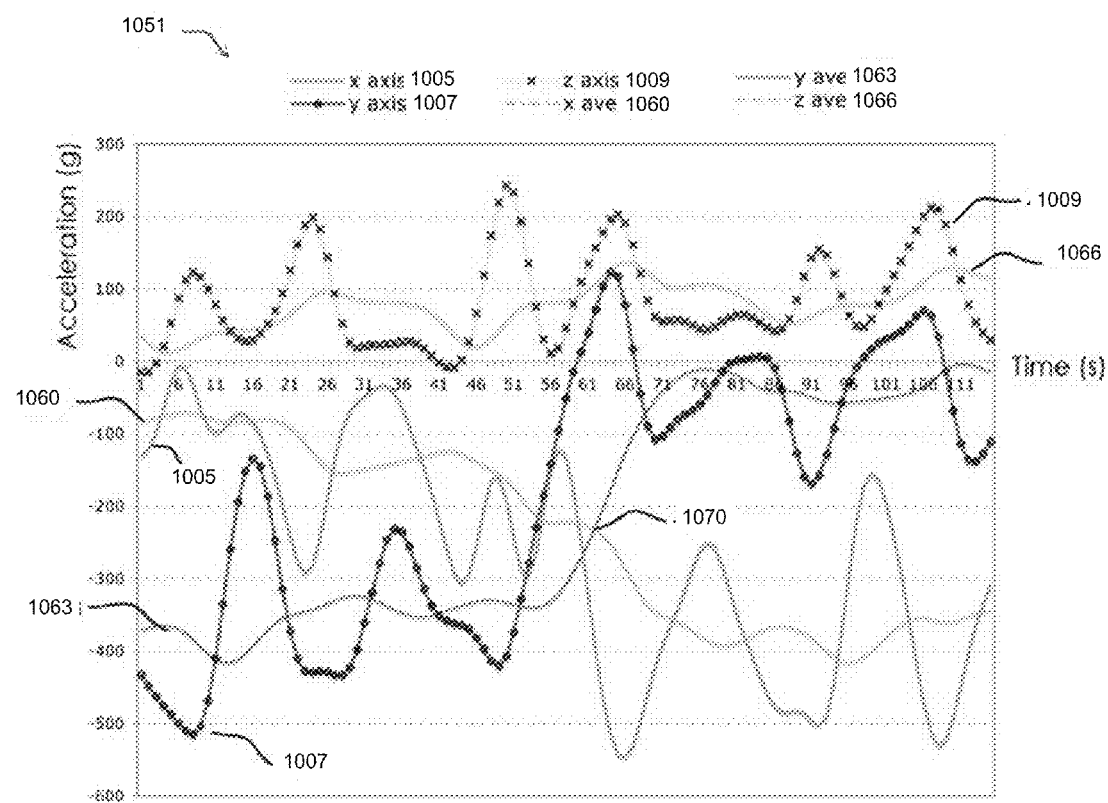

FIG. 10B illustrates a second gravitational influence graph 1051 for the same data set as shown in FIG. 10A over a rolling average sample period of 1 second. FIG. 10B shows a second x-axis rolling average 1060, a second y-axis rolling average 1063 and a second z-axis rolling average 1066. As shown, a second point of intersection 1070 occurs between the second x-axis rolling average 1060 and second y-axis rolling average 1063 much earlier in time than the first point of intersection 1022. The earlier point of intersection more accurately reflects the time when rotation actually occurs. As shown by FIGS. 10A and 10B, a change in the length of the sample period for the rolling average can greatly affect the sensitivity of the device to changes in orientation.

In one embodiment, the gravitational influence logic 707 calculates the total gravity caused acceleration based upon the acceleration on each axis. The gravitational influence logic 707 in one embodiment then assigns a percentage of the total acceleration to each axis. From the percentage of total acceleration on the axes the gravitational influence logic 707 then calculates the approximate device orientation.

Referring back to FIG. 7, the dominant axis logic 710 assigns a dominant axis based upon the gravitational influence. In one embodiment, the actual axis with the largest absolute rolling average over the sample period is assigned as the dominant axis. In this embodiment, the dominant axis therefore corresponds to the axis having the largest absolute rolling average at a given time. In an alternative embodiment, the dominant axis does not correspond to one of the actual axes of the accelerometer in its current orientation, but rather to an axis that is defined as aligned to gravity.

Figure 11:
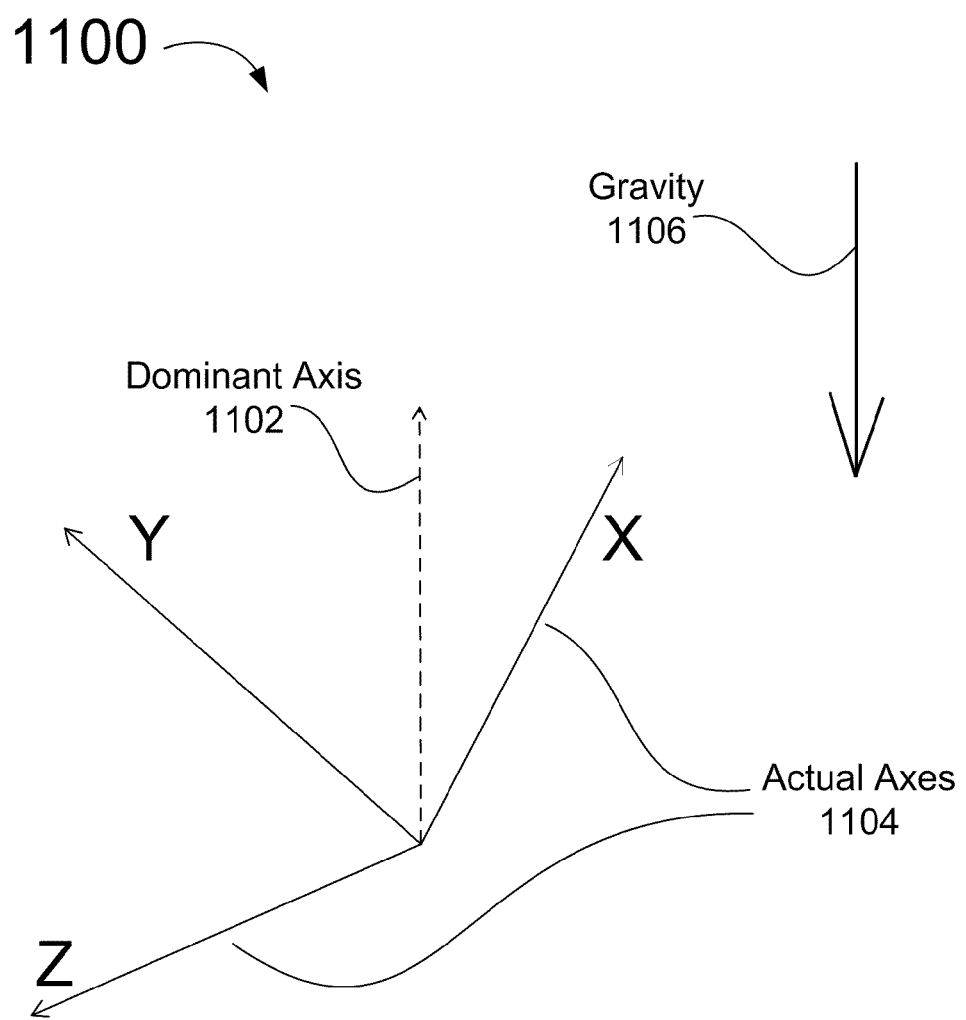
FIG. 11 illustrates a plan view of a dominant axis that does not correspond to an actual axis.

FIG. 11 illustrates a plan view 1100 of an exemplary dominant axis 1102 that does not correspond to one of the actual axes 1104 of an accelerometer. The dominant axis 1102, as shown in FIG. 11, can be a component of the x axis, y axis, and/or z axis, and is approximately aligned with gravity 1106. In one embodiment, the dominant axis 1102 corresponds to a virtual axis that is a component of a virtual coordinate system. The relationship between the virtual coordinate system and the actual coordinate system can be determined by performing a coordinate transformation. In one embodiment, the virtual coordinate system is a virtual Cartesian coordinate system, in which the dominant axis is one of a virtual x-axis, y-axis or z-axis. In alternative embodiments, the dominant axis 1102 is a virtual axis of, for example, a polar coordinate system.

In one embodiment, the dominant axis logic 710 assigns the dominant axis by performing a true gravity assessment. A true gravity assessment may be performed by doing trigonometric calculations on the actual axes based on the gravitational influence. For example, the arcsine function can determine the exact angle between the actual axes and the gravitational influence. True gravity assessments can exactly align the dominant axis with the gravitational influence, but can be resource expensive.

In one embodiment, the dominant axis logic 710 assigns the dominant axis by comparing the gravitational influence to a lookup table. A lookup table provides greater accuracy than assigning the dominant axis to the axis that has the largest acceleration, and is less resource expensive than calculating the exact gravitational influence on each axis. A lookup table divides accelerations into known limits that define a probability range in which gravity is acting.

Figure 12:
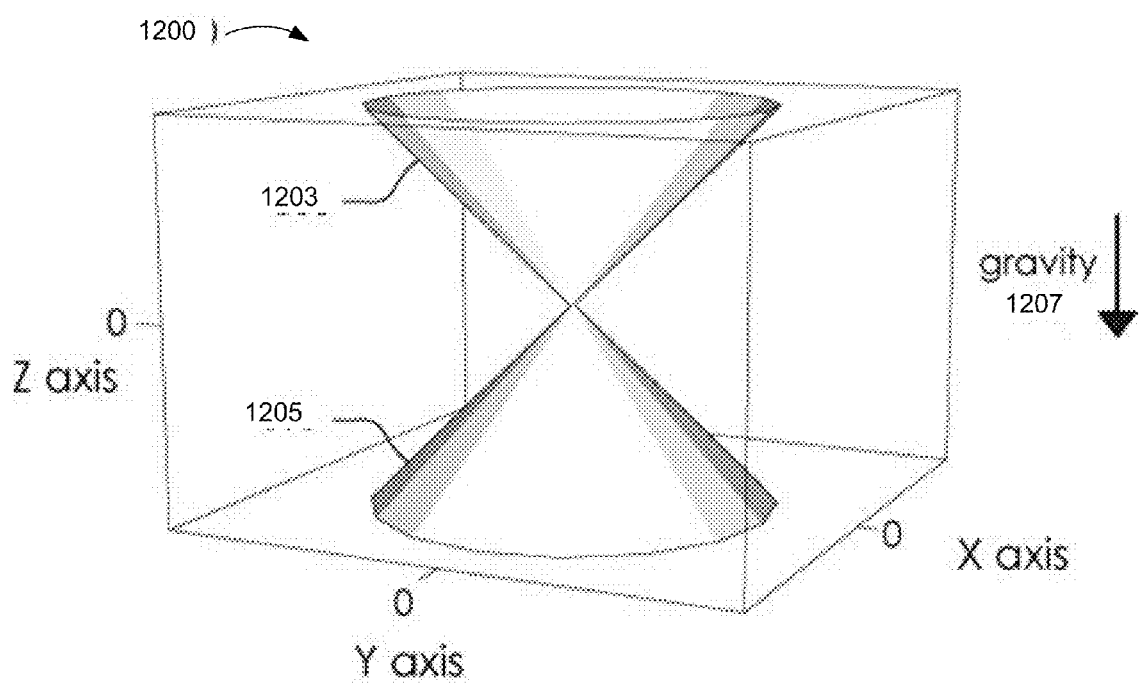
FIG. 12 illustrates an exemplary probability range represented by a plurality of cones.

FIG. 12 illustrates an exemplary probability range 1200 represented by a plurality of projections, each of the projections corresponding to an entry on a lookup table. In the illustrated embodiment, the area of space swept by the projections defines a cone. In alternative embodiments, the area of space swept by the projections defines other shapes. The lookup table that corresponds to the exemplary probability range 1200 has six entries, each of which corresponds to a projection having an included angle between opposite sides of ninety degrees. For example, if the gravitational influence acts within the first projection 1203, then the table entry that corresponds to that projection is assigned as the dominant axis. The same applies to the second projection 1205, and the other projections (not illustrated). As shown, the dominant axis is assigned to the table entry corresponding to the second projection 1205 because it is aligned with and in the direction of the force of gravity 1207. In alternative embodiments, the dominant axis is assigned to the table entry corresponding to the projection that is aligned with and in the opposite direction of the force of gravity 1207.

Returning to FIG. 7, in one embodiment, the motion recognition logic 120 detects gestures and/or steps by utilizing data regarding the dominant axis. In one embodiment, certain gestures and/or steps are detected by utilizing the acceleration along only the dominant axis. In other embodiments, acceleration along other axes may also be used and/or acceleration along only the non-dominant axes may be used. In one embodiment, the dominant axis assignment is used to determine whether a step and/or gesture recognition cycle should be started. In one embodiment, certain gestures may only be detected when the dominant axis corresponds to a particular axis when the gesture is started. After the certain gestures have begun, assignment of the dominant axis may be unimportant to continue the gesture recognition.

Figure 13:
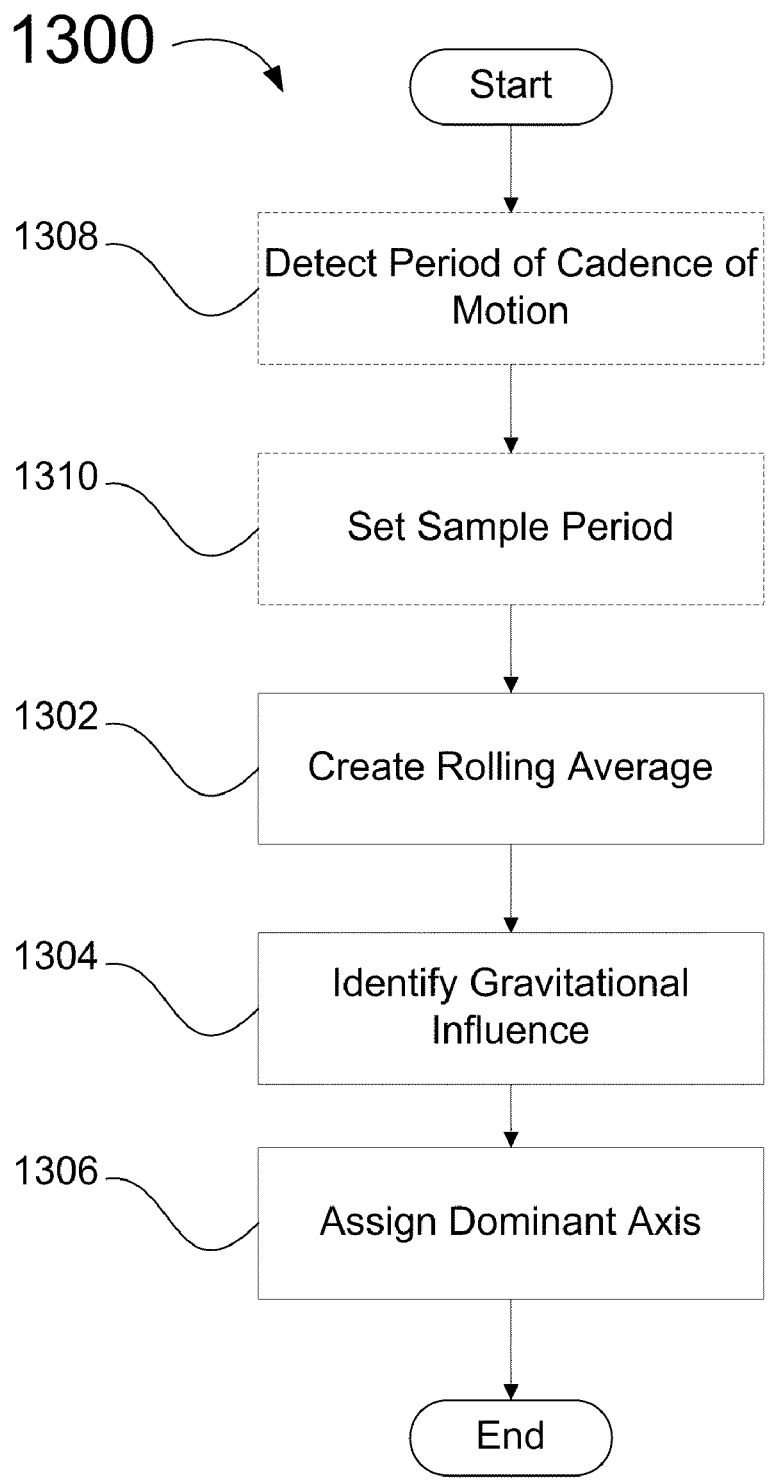
FIG. 13 shows a processing diagram for a method of determining an orientation of an accelerometer in accordance with one embodiment of the present invention.

FIG. 13 shows a processing diagram 1300 for a method of determining an orientation of an accelerometer, in accordance with one embodiment of the present invention. In one embodiment, determining an orientation of the accelerometer determines an orientation of a device that includes the accelerometer.

At processing block 1302, one or more rolling averages of accelerations are created over a sample period. The rolling averages can be simple rolling averages or weighted rolling averages such as exponential rolling averages. In an exponential rolling average, recent data is weighed more heavily relative to old data. The weighting applied to the most recent price depends on the specified period of the rolling average. The shorter the period, the more weight that will be applied to the most recent measurement. This can cause the rolling average to react more quickly to changing conditions.

The sample period over which the rolling averages are created can be pre-configured, adjusted based upon applications being used, user selected, or determined dynamically. In one embodiment, two or more rolling averages of accelerations are created concurrently along the same axes. The concurrent rolling averages can have different sample periods.

In one embodiment, if the sample period over which creation of the rolling averages of accelerations is determined dynamically, a period of a cadence of motion is detected at processing block 1308. Subsequently, a sample period is set at processing block 1310 based upon the period of the cadence of motion. In one embodiment, the sample period is set such that it has at least the period of the cadence of motion. In one embodiment, the sample period is set to a multiple of the period of the cadence of motion. In one embodiment, periods can be determined for multiple cadences of motions at processing block 1308, and sample periods can be set for each determined cadence of motion. This embodiment facilitates the concurrent creation of two or more rolling averages of accelerations over different sample periods.

In one embodiment, the orientation of the accelerometer is determined based upon the rolling average or averages of accelerations. In one embodiment, determining the orientation of the accelerometer further includes identifying a gravitational influence based on the rolling averages of accelerations and determining the orientation, compared to the X-Y-Z axes of the accelerometer.

At processing block 1304, a gravitational influence is identified based upon the rolling average of accelerations. In one embodiment, the gravitational influence is identified by calculating the total acceleration based upon the acceleration on each axis. In such an embodiment, a percentage of the total acceleration can then be assigned to each axis and an approximate device orientation can be determined. At processing block 1306, a dominant axis is assigned based upon the gravitational influence.

The present invention may be performed by hardware components or may be embodied in machine-executable instructions, which may be used to cause a general-purpose or special-purpose processor programmed with the instructions to perform the method described above. Alternatively, the method may be performed by a combination of hardware and software.

The present invention may be provided as a computer program product, or software, that may include a machine-readable medium having stored thereon instructions, which may be used to program a computer system (or other electronic devices) to perform a process according to the present invention. The machine-readable medium may include, but is not limited to, floppy diskettes, optical disks, CD-ROMs, and magneto-optical disks, ROMs, RAMs, EPROMs, EEPROMs, magnetic or optical cards, flash memory, or other type of media or machine-readable mediums suitable for storing electronic instructions.

In the foregoing description, numerous specific details have been set forth such as examples of specific systems, languages, components, etc. in order to provide a thorough understanding of the present invention. It will be apparent, however, to one skilled in the art that these specific details need not be employed to practice the present invention. In other instances, well known materials or methods have not been described in detail in order to avoid unnecessarily obscuring the present invention.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A machine-accessible medium including data that, when accessed by a machine, cause the machine to perform a method comprising:
   monitoring accelerations from an inertial sensor disposed in a chest strap, the inertial sensor having a plurality of axes;
   processing the accelerations to determine one or more user activity statistics, the processing comprising:
      creating a rolling average of accelerations for each of the plurality of axes;
      comparing a value of the rolling average of accelerations for a first axis to values of the rolling averages of accelerations for one or more additional axes of the plurality of axes; and
      assigning a dominant axis based upon relative values of the rolling averages of accelerations;
   formatting the user activity statistics to a generic format understandable by a plurality of devices; and
   transmitting the generically formatted user activity statistics from the chest strap to an electronic device.

2. The machine-accessible medium of claim 1, the method further comprising:
   monitoring one or more additional metrics from one or more additional sensors; and
   correlating the additional metrics to the one or more user activity statistics.

3. The machine-accessible medium of claim 1, wherein the user activity statistics include at least one of a breathing rate, a current user activity, a count of periodic human motions for the current user activity, a total distance traveled, vertical distance traveled, a current speed, an average speed, calories burned, heart rate, and a user orientation to gravity.

4. The machine-accessible medium of claim 1, wherein the formatted user activity statistics are transmitted wirelessly.

5. The machine-accessible medium of claim 1, wherein the generic format is an XML format.

6. The machine-accessible medium of claim 1, the method further comprising:
   providing user feedback based on the user activity statistics, the user feedback including at least one of aural, visual and tactile feedback.

7. The machine-accessible medium of claim 1, wherein the user feedback includes at least one of an indication to speed up and an indication to slow down.

8. The machine-accessible medium of claim 1, wherein processing accelerations includes determining information regarding a user's gait, the information including at least a comparison between right foot and left foot activity.

9. The machine-accessible medium of claim 1, the method further comprising:
   determining whether the chest strap has been properly positioned on a user's body based at least in part on the dominant axis.

10. The machine-accessible medium of claim 1, wherein another of the user activity statistics is a periodic human motion count that is determined using only accelerations along the dominant axis.

11. The machine-accessible medium of claim 1, wherein the chest strap is to be positioned on a user's body such that the inertial sensor is located approximately along an axis of symmetry of the user's body, the method further comprising:
   differentiating between first accelerations caused by motions from a right half of the user's body and second accelerations caused by motions from a left half of the user's body.

12. An inertial sensor based device, comprising:
   a chest strap;
   an inertial sensor disposed in the chest strap to monitor accelerations along a plurality of axes;
   a processor disposed in the chest strap and coupled to the inertial sensor to process the accelerations to determine one or more user activity statistics, the processing comprising:
      creating a rolling average of accelerations for each of the plurality of axes;

comparing a value of the rolling average of accelerations for a first axis to values of the rolling averages of accelerations for one or more additional axes of the plurality of axes; and assigning a dominant axis based upon relative values of the rolling averages of accelerations;

the processor further to format the user activity statistics to a generic format understandable by a plurality of devices; and a transmitter disposed in the chest strap to transmit the generically formatted user activity statistics from the chest strap to an electronic device.

13. The inertial sensor based device of claim 12, further comprising:
   a memory to store at least one of the accelerations and the user activity statistics.

14. The inertial sensor based device of claim 12, further comprising:
   one or more feedback elements, each of the one or more feedback elements to provide at least one of aural, visual and tactile feedback.

15. The inertial sensor based device of claim 12, further comprising:
   one or more additional sensors to provide one or more additional metrics to correlate to the one or more user activity statistics.

16. The inertial sensor based device of claim 12, wherein the user activity statistics include at least one of a breathing rate, a current user activity, a count of periodic human motions for the current user activity, a total distance traveled, vertical distance traveled, a current speed, an average speed, calories burned, heart rate, and a user orientation to gravity.

17. The inertial sensor based device of claim 12, wherein the transmitter is a wireless transmitter.

18. The inertial sensor based device of claim 12, wherein the generic format is an XML format.

19. The inertial sensor based device of claim 12, wherein the chest strap is configured to be positioned on a user's body such that the inertial sensor is approximately located along an axis of symmetry on a user's body, the inertial sensor based device further comprising:
   where the processor differentiates between first accelerations caused by motions from a right half of the user's body and second accelerations caused by motions from a left half of the user's body.

20. An inertial sensor based device, comprising:
   a chest strap;
   an inertial sensor disposed in the chest strap to monitor accelerations along a plurality of axes; and
   a processor disposed in the chest strap and coupled to the inertial sensor to process the accelerations to determine one or more user activity statistics, the processing comprising:
      creating a rolling average of accelerations for each of the plurality of axes;
      comparing a value of the rolling average of accelerations for a first axis values of the rolling averages of accelerations for one or more additional axes of the plurality of axes; and
      assigning a dominant axis based upon relative values of the rolling averages of accelerations.

* * * * *